United States Patent [19]

Holzner

[11] Patent Number: 5,170,886
[45] Date of Patent: Dec. 15, 1992

[54] PLASTIC MULTICOMPARTMENT PACKAGE FOR SOLID AND LIQUID PRODUCTS

[75] Inventor: Günter Holzner, Grand-Lancy, Switzerland

[73] Assignee: Firmenich S.A., Geneva, Switzerland

[21] Appl. No.: 790,629

[22] Filed: Nov. 12, 1991

[30] Foreign Application Priority Data

May 12, 1990 [CH] Switzerland .................. 3846/90

[51] Int. Cl.⁵ .......................................... F17G 13/00
[52] U.S. Cl. ........................... 206/0.5; 206/524.8; 206/823; 239/55
[58] Field of Search ............. 206/0.5, 823, 524.8; 239/43, 53, 55, 56

[56] References Cited

U.S. PATENT DOCUMENTS

| | | | |
|---|---|---|---|
| 3,578,545 | 5/1971 | Carson et al. | 239/56 X |
| 3,717,303 | 2/1973 | Daeninckx et al. | 206/0.5 |
| 4,161,283 | 7/1979 | Hyman | 239/55 |
| 4,285,468 | 8/1981 | Hyman | 239/55 |
| 4,576,283 | 3/1986 | Fafournoux | 206/524.8 |
| 4,634,614 | 1/1987 | Holzner | 239/55 |
| 4,798,288 | 1/1989 | Holzner | 206/222 |

FOREIGN PATENT DOCUMENTS 2201305 7/1973 Fed. Rep. of Germany.
2539492 7/1984 France.

Primary Examiner—William I. Price
Attorney, Agent, or Firm—Pennie & Edmonds

[57] ABSTRACT

A package consisting of a hermetically sealed ensemble in plastic material, under vacuum, intended for containing devices for perfuming or purifying ambient air or closed spaces, said devices having a wall of polymeric material for diffusing active odoriferous substances, the package being characterized in that said devices therein-contained are joined side by side by superposition, under subatmospheric pressure, of the surfaces of their diffusion walls.

16 Claims, 4 Drawing Sheets

5,170,886

PLASTIC MULTICOMPARTMENT PACKAGE FOR SOLID AND LIQUID PRODUCTS

BRIEF SUMMARY OF THE INVENTION

The present invention relates to a plastic hermetically sealed package, under vacuum, having resilient walls, intended for containing devices for perfuming or purifying ambient air or closed spaces, said devices having a polymeric wall enabling the diffusion of an active odoriferous or deodorant substance into the surrounding environment, which package is characterized in that said devices contained in the package are joined side by side by superposition, under subatmospheric pressure, of the surfaces of their polymeric diffusion walls, said pressure being applied inside the package containing said devices when said resilient walls are sealed.

BACKGROUND OF THE INVENTION

International patent application WO 81/00051, published on Jan. 22, 1981, describes an article impervious to liquids intended for perfuming ambient air or closed spaces, characterized in that it contains a perfuming composition enriched in weak polarity substances, odoriferous or not, and in that it possesses at least one polymeric wall enabling the diffusion towards the exterior of active odorant ingredients.

French patent application FR-A 2 091 855, published Jan. 21, 1972, discloses a device for the continuous diffusion of vapors from purifying agents, which comprises a permeable wall in macromolecular material, one face of which is in contact with the volatile purifying agent, the latter impregnating a fibrous mass which is covered by the permeable wall.

French patent application FR-A 2 336 946, published Jul. 29, 1977, relates to a slow diffusion air-freshening system which comprises an enclosure and a perfume contained in said enclosure, at least one surface of said enclosure being a polymer film. Also in this system, the perfume is impregnated on a support such as silica, talc, glasswool or blotting paper.

U.S. Pat. No. 3,578,545, published May 11, 1971, discloses a flexible stratified device releasing a perfume and comprising a perfume impregnated fabric, enclosed in a porous plastic film, permeable to the perfume vapors.

U.S. Pat. No. 4,161,283, published Jul. 17, 1979, describes a device intended for the continuous diffusion of purifying vapors; said device comprises an exterior wall formed of a polymeric material allowing a molecular diffusion and an impermeable interior wall. The exterior wall is also covered by an impermeable sheet capable of preventing the diffusion of the active volatile substances during storage.

An analogous device is described in U.S. Pat. No. 4,285,468, published Aug. 25, 1981.

Since the purifying or freshening articles described in the prior art consist all of a system comprising a polymeric diffusion wall, they must posses a device intended for preventing the diffusion of the active perfuming substances into the environment during storage.

To this end, International patent application WO 81/00051 describes a means consisting in the application of a polymeric sheet of the Surlyn ® type (origin: Du Pont de Nemours) onto the walls through which diffusion normally occurs. Such a polymeric sheet may be made to cling through thermal welding to polyethylene or polypropylene and be pulled off just before use.

Another means to the same end is the use of aluminium sheets welded to polypropylene foam.

A problem rises however upon long storage of such devices before sale: owing to the diffusion of the perfume vapors through the polymeric material walls of the package, considerable loss of the initial amount of active substance has been observed. In order to obviate this disadvantage, a multi-chamber device has been developed by the instant applicant (see International patent application WO 82/02700, published Aug. 19, 1982). In a device of this type, the active perfuming solution is kept in a compartment whose walls are impermeable to the perfume vapors and which has a joint that can be broken under the effect of an external pressure. Just before use, once the walls of said joint are broken, the solution passes into a compartment whose walls are made of a polymeric material permeable to the perfume vapors which can then diffuse evenly into the surrounding atmosphere.

Such a device is very efficient in practice, but its manufacture requires a sophisticated apparatus and a rigorous assembling technique.

Patent application FR-A 2 539 492 proposes, as a remedy to such inconvenients, a novel solution based on a simple technique. It describes, in effect a direct assemblage by welding of a thin paper layer to the external wall of the polymeric membrane through which diffuse the vapors of the active substance. This thin paper layer is then covered by a polymeric material sheet, for example a material of the Surlyn ® type, polyethylene-based, on which is finally welded a metallic sheet, preferably for example an aluminum sheet.

THE INVENTION

The present invention brings a novel solution to the problem of the packaging of devices permeable to volatile substances. It relates to a plastic hermetically sealed package, under vacuum, having resilient walls, intended for containing devices for perfuming or purifying ambient air or closed spaces, said devices having a polymeric wall enabling the diffusion of an active odoriferous or deodorant substance into the surrounding environment, which package is characterized in that said devices contained in the package are joined side by side by superposition, under subatmospheric pressure, of the surfaces of their polymeric diffusion walls, said pressure being applied inside the package containing said devices when said resilient walls are sealed.

The above-described package is particularly easy to produce and can be manufactured by means of current industrial equipment. It is a cheap and ready-to-use package (single dose) which guaranties that the active solution can be kept without any losses for long periods of time before use. On the other hand, at the desired moment, the user can easily tear the package, either partially or entirely, extract the diffusion devices and thus activate the diffusion of the vapors of the active substance towards the exterior. In effect, when the package is opened, its internal pressure is balanced by the surrounding pressure, thus provoking simultaneous separation of the devices originally joined side by side, and their respective diffusion walls are then exposed to the air. The diffusion phenomenon can then start.

DESCRIPTION OF THE DRAWINGS

Particular embodiments of the package according to the invention will now be described, by way of example, with reference to the attached drawings wherein.

Figure 1:
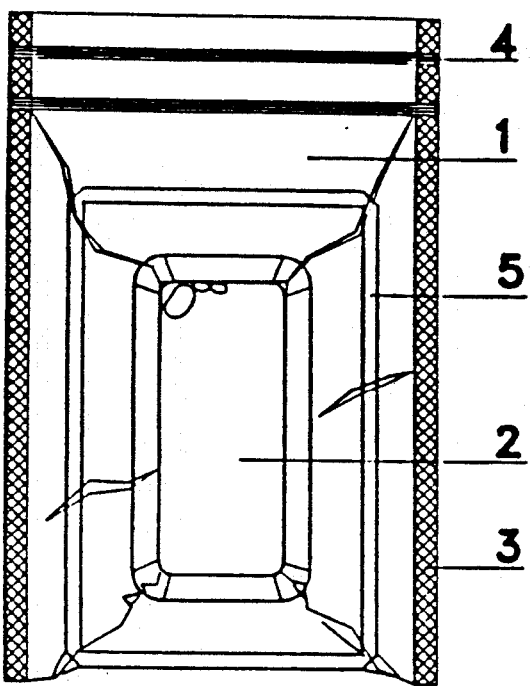
FIG. 1 is a plane view of a package comprising two diffusion devices, together with the corresponding cross-section and longitudinal expanded view.
Figure 1:
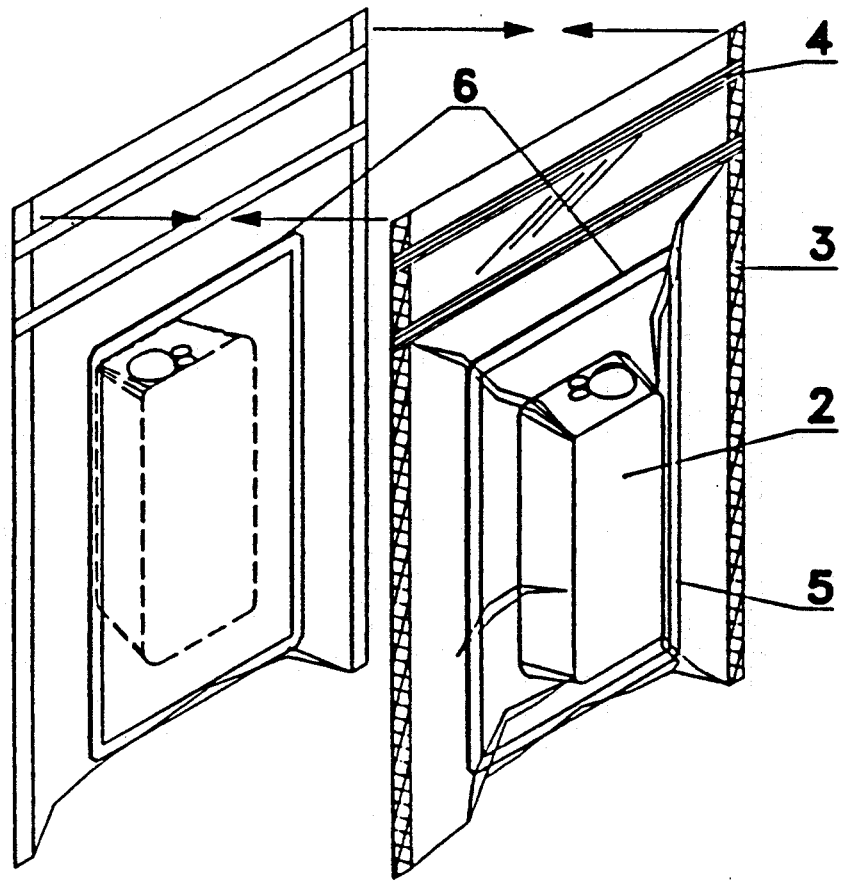

Package 1 represented in FIG. 1 consists of two paired devices 2, joined side by side by superposition of the surfaces of their polymeric walls 6. Each device comprises an edge 5 created by the welding of the polymeric diffusion wall to a thermally formed shell. The two devices are kept in a hermetically sealed bag which is formed by assembling together two polymeric sheets through welding of their peripheric edges so as to form the tearable joints 3 and 4.

In the view shown in FIG. 1, the two devices are filled with a deodorant or purifying liquid substance.

Figure 2:
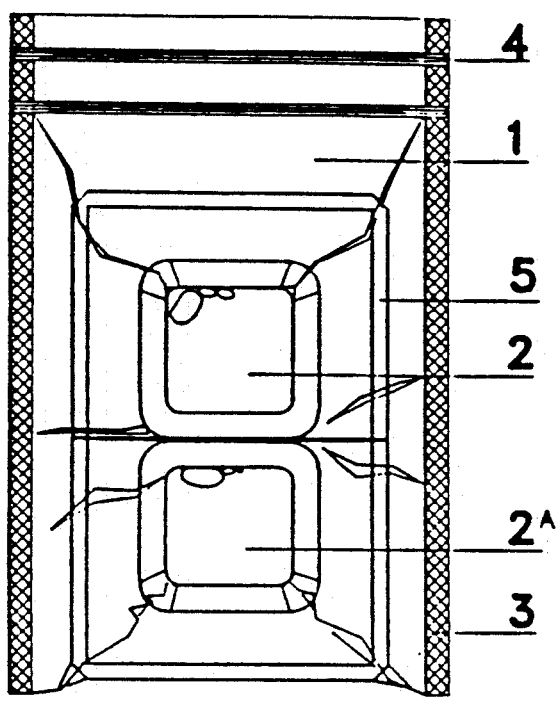
FIG. 2 is a plane view of a package comprising three diffusion devices, together with the corresponding cross-section and longitudinal expanded view.
Figure 2:
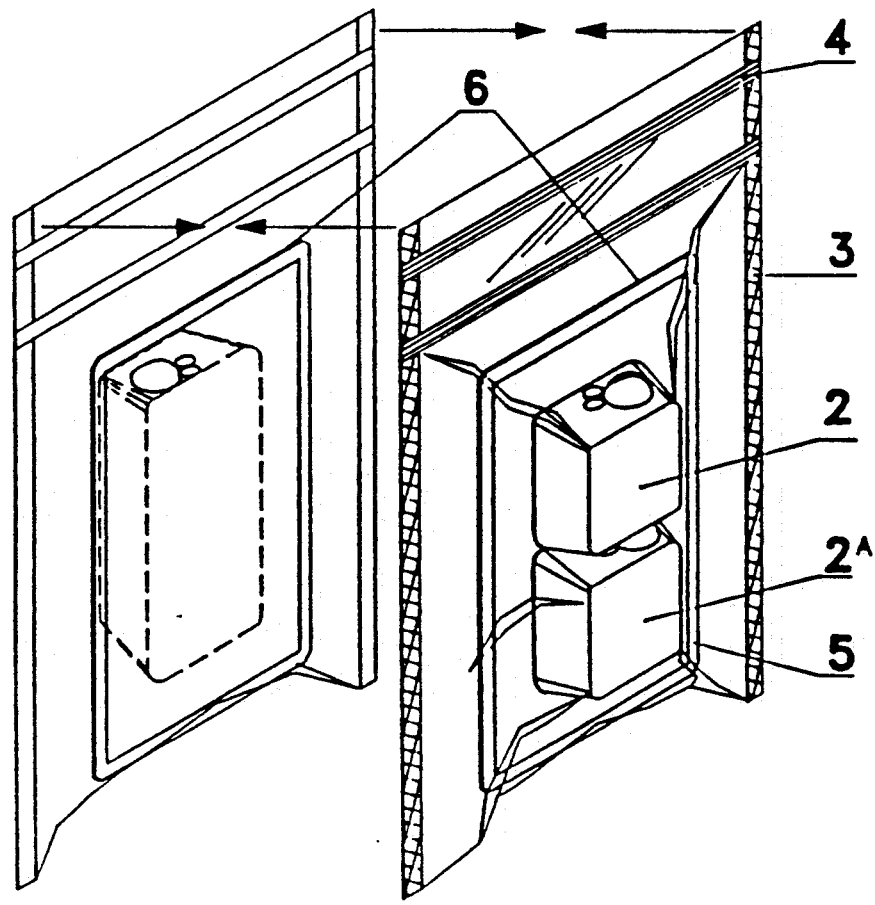

FIG. 2 represents a particular embodiment of the package according to the invention. There are three devices 6 containing the active substance. The two devices 2 and 2A are assembled in series and their content is inferior to that of the device to which they are joined side by side. The two devices of lower volume can be separated by the user thanks to an indentation or welded joint in the medium region.

Figure 3:
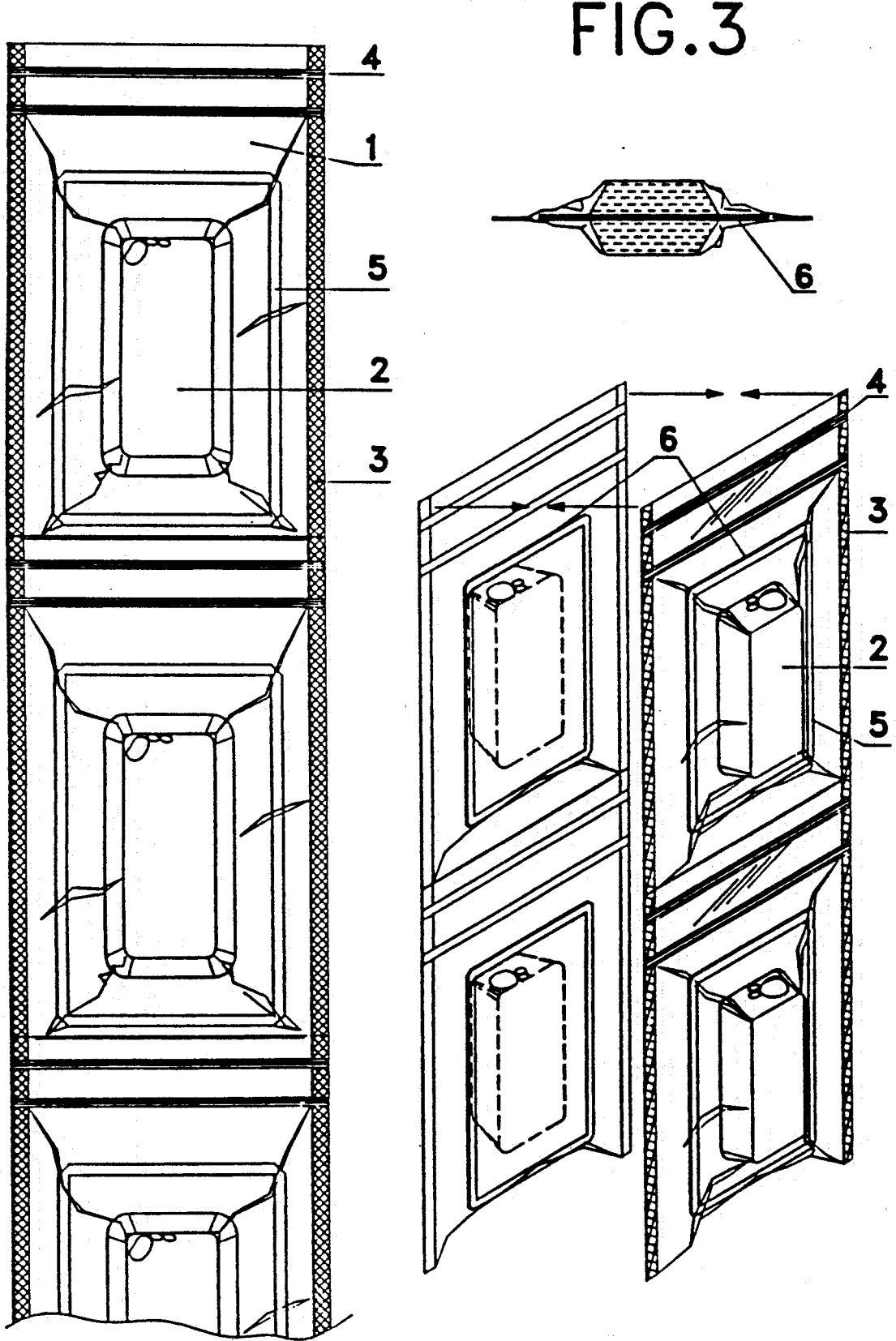
FIG. 3 is a plane view of a package comprising a series of paired diffusion devices, together with the corresponding cross-section and longitudinal expanded view.

FIG. 3 represents a package 1 comprising a series of paired devices 2 in an embodiment analogous to that of FIG. 1. Such devices can be activated by tearing the package along the welding edges 3 and 4 or by cutting across said package.

Figure 4:
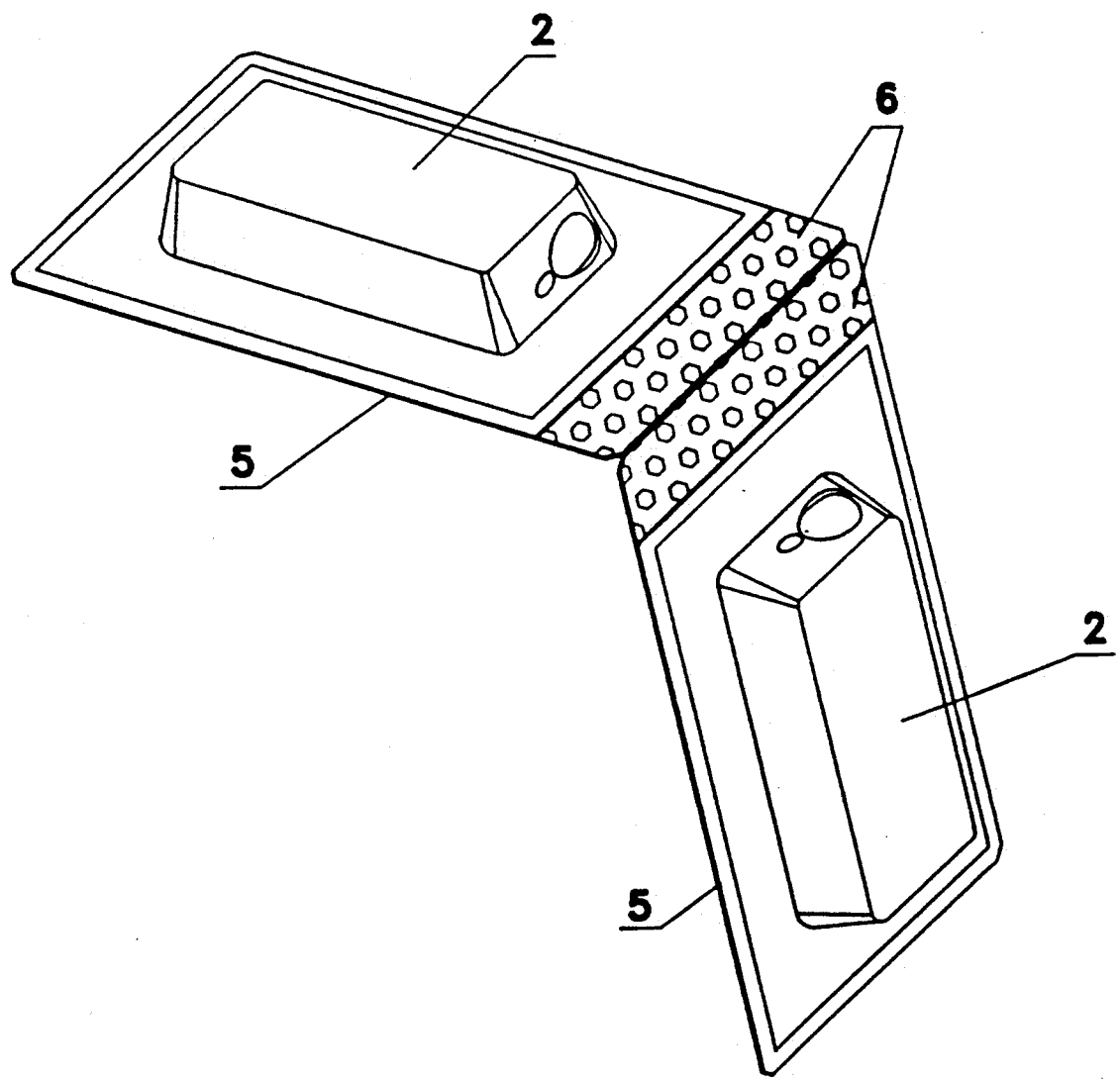
FIG. 4 is a perspective view of two diffusion devices welded together through the upper portion of their walls.

FIG. 4 shows a particular arrangement of two diffusion devices 2 welded together through the upper edge of their polymeric walls 6, before being placed in the hermetic bag.

Activation of the devices takes place through exposure to the air of the polymeric diffusion walls when the package is opened and the two parts joined side by side separate, as is shown by the expanded view along a longitudinal axis given in FIGS. 1 to 3.

For other possible embodiments of the package according to the invention, the reader is referred to the particular devices described in the prior art.

The major advantage of the package according to the invention resides both in the simplicity of its assemblage and in the particularly neat manner in which it can be activated. Since the diffusion devices are coupled at least by two, it is clear that at least two devices are simultaneously activated. These two devices can be used either jointly, for perfuming the same room or closed space, or separately. It goes without saying that the specific form of these devices, and in particular their capacity, can vary as a function of their intended use. However, a remaining critical aspect of the invention is the fact that such devices require a polymeric diffusion wall having a substantially plane surface, so that their superposition under vacuum may allow as flawless a temporary adhesion as possible, and this until the package is opened.

For the manufacture of such devices, the reader is particularly referred to the prior art documents already mentioned above. The diffusion wall can thus be formed of sheets of varied polymeric materials such as those described in International patent application WO 81/00051.

Since the coupling or adhesion of the devices inside the package takes place as a result of a purely physical phenomenon, without resorting to the use of adhesives, the diffusion of the vapors of the active substance is in no way hampered. The most elementary embodiment of the invention is a package comprising only two devices or reservoirs containing the active substance. However, it goes without saying that such a package may contain an undetermined number of devices, the only restriction being that said devices must be joined by direct and full contact of their respective diffusion walls. Thus, the package may contain an even number of identical devices, said devices being then arranged pairwise. In the case where the package contains devices having non-identical diffusion wall surfaces, it will be necessary to ensure that the package is assembled in such a way that device "A" is joined side by side to a number of devices n×"B" (n being an integer), the sum of the surfaces of the diffusion walls of the latter being equal to the surface of the diffusion wall of device "A". Premature diffusion of the vapors of the active substance, before activation by the user, is thus entirely suppressed.

Preferably, the package is sealed by simple welding of the edges of the polymeric sheets forming its walls. The sealing takes place under vacuum, thus applying a subatmospheric pressure, for example of the order of a few millimeters of mercury. This is a perfectly current technique, frequently used for example in the food packaging industry, whenever it is desired to ensure long-lasting preservation of foods, namely those which are subsequently frozen. Welding temperatures can generally vary between 150° and 220°. Obviously, the latter are a function of the nature of the polymeric material used. In order to facilitate its opening, the package may comprise indentations or notches at one of its extremities, or even a nail-groove allowing easier separation of the sheets forming the walls of the package.

MANUFACTURING OF THE PACKAGE

Devices intended for perfuming or purifying ambient air or closed spaces were manufactured as follows.

A composite sheet of 250 μm Barex (registered trademark of BP Chemicals; polyacrylonitrile) and 50 μm polyethylene was thermally formed by means of a specific mould to impart to it the desired form and dimension (apparatus: Thermoforming Spa, Milan). The transparent shell thus obtained was then joined by welding to the polymeric membrane forming the flat diffusion wall of the device, while leaving nevertheless an overture intended for filling in the perfuming or purifying substance. The volume of the chamber can vary as a function of the intended use, in particular as a function of the desired or predicted period of activity. In practice, it was observed that devices able to contain between 3 and 15 cc were perfectly convenient in most cases. The membrane is preferably formed by a copolymer sheet consisting of polyethylene and polyethylacrylate, for example 82:18. The welding apparatus was of the Fermant 400 type (Joisten & Kettenbaum GmbH, Bensberg-Herkenrath, Germany). Once the chamber thus formed has been filled with the active perfuming or purifying substance, it is sealed by welding. The thus obtained devices are then introduced into a bag consisting of two polymeric multilayer sandwich sheets (ex:- polyamide and polyethylene) having three of their edges welded together, and are joined side by side in such a way as to oppose their diffusion walls face to face. The bag is then introduced into a welding apparatus equipped with a sucking system (ex: VC 999 type, Inauen Maschinen AG, Herisau, Switzerland). A vacuum of 1-2 mmHg and a temperature of 180°-220° C. are applied, resulting in the hermetic sealing of the bag while provoking a perfect contact between the diffusion walls of the devices contained in the bag.

What I claim is:

1. A plastic hermetically sealed package, under vacuum, having resilient walls, intended for containing devices for perfuming ambient air or closed spaces, said devices having a polymeric wall enabling the diffusion of an active odoriferous substance into the surrounding environment, which package is characterized in that said devices contained in the package are joined side by side by superposition, under subatmospheric pressure, of the surfaces of their polymeric diffusion walls, said pressure being applied inside the package containing said devices when said resilient walls are sealed.

2. A package according to claim 1, containing an even number of devices for perfuming ambient air or closed spaces and wherein said devices are joined pairwise.

3. A package according to claim 1, containing two devices for perfuming ambient air or closed spaces.

4. A package according to claim 1, wherein said polymeric diffusion walls of said perfuming devices are formed of a simple polymeric material covered with a thin paper layer.

5. A package according to claim 1, wherein activation of said devices takes place when the package is opened, its internal pressure being balanced by the pressure of the surroundings, and the devices separate, their diffusion walls being thus exposed to the air such that slow evaporation of the perfuming substance contained in said devices results.

6. A package according to claim 1, wherein said resilient walls are formed of sheets of polymeric material derived from one of a polyester or a polyamide.

7. A package according to claim 1, wherein said polymeric diffusion walls of said perfuming devices are formed of composite polymeric material covered with a thin paper layer.

8. A package according to claim 1, wherein said resilient walls are formed of sheets of polymeric material derived from sandwich multilayer sheets of one of a polyester or a polyamide with polyethylene.

9. A plastic hermetically sealed package, under vacuum, having resilient walls, intended for containing devices for purifying ambient air or closed spaces, said devices having a polymeric wall enabling the diffusion of an active deodorant substance into the surrounding environment, which package is characterized in that said devices contained in the package are joined side by side by superposition, under subatmospheric pressure, of the surfaces of their polymeric diffusion walls, said pressure being applied inside the package containing said devices when said resilient walls are sealed.

10. A package according to claim 9, containing an even number of devices for purifying ambient air or closed spaces and wherein said devices are joined pairwise.

11. A package according to claim 9, containing two devices for purifying ambient air or closed spaces.

12. A package according to claim 9, wherein said polymeric diffusion walls of said purifying device are formed of a simple polymeric material covered with a thin paper layer.

13. A package according to claim 9, wherein activation of said devices takes place when the package is opened, its internal pressure being balanced by the pressure of the surroundings, and the devices separate, their diffusion walls being thus exposed to the air such that slow evaporation of the purifying substance contained in said devices results.

14. A package according to claim 9, wherein said resilient walls are formed of sheets of polymeric material derived from sandwich multilayer sheets of one of a polyester or a polyamide with polyethylene.

15. A package according to claim 9, wherein said resilient walls are formed of sheets of polymeric material derived from one of a polyester or a polyamide.

16. A package according to claim 9, wherein said resilient walls are formed of sheets derived from sandwich multilayer sheets of one of a polyester or a polyamide with polyethylene.

* * * * *